United States Patent [19]

Perkins

[11] Patent Number: 5,370,112
[45] Date of Patent: Dec. 6, 1994

[54] METHOD AND MEANS FOR POWERING PORTABLE OXYGEN SUPPLY SYSTEMS

[75] Inventor: Warren E. Perkins, Jensen Beach, Fla.

[73] Assignee: DeVilbiss Health Care, Inc., Somerset, Pa.

[21] Appl. No.: 85,774

[22] Filed: Jul. 1, 1993

[51] Int. Cl.⁵ ............................................. A61M 15/00
[52] U.S. Cl. ............................ 128/204.21; 222/250; 128/204.26; 320/61
[58] Field of Search .............. 320/61, 62, 64; 322/3, 322/11, 100; 222/249, 250, 251; 128/204.21, 204.26, 205.18, 201.23, 204.24, 204.23, 204.25, 204.29, 205.24, 205.14, 205.13, 205.16

[56] References Cited

U.S. PATENT DOCUMENTS

| | | |
|---|---|---|
| 2,479,699 | 8/1949 | Powell . |
| 3,507,580 | 4/1970 | Howard et al. . |
| 3,612,979 | 10/1971 | Roth . |
| 3,801,841 | 4/1974 | Hall . |
| 3,921,052 | 11/1975 | Milano ................................. 320/61 |
| 3,927,366 | 12/1975 | Mulier et al. . |
| 4,249,096 | 2/1981 | Hickox . |
| 4,462,398 | 7/1984 | Durkan et al. ................. 128/200.14 |
| 4,705,034 | 11/1987 | Perkins ........................... 128/204.21 |
| 4,918,369 | 4/1990 | Solorow ................................ 322/35 |
| 5,005,570 | 4/1991 | Perkins ........................... 128/204.23 |

FOREIGN PATENT DOCUMENTS

| | | | |
|---|---|---|---|
| 7710239 | 7/1979 | Sweden ................................. 320/61 |

*Primary Examiner*—Edgar S. Burr
*Assistant Examiner*—Eric P. Raciti
*Attorney, Agent, or Firm*—MacMillan, Sobanski & Todd

[57] ABSTRACT

Portable gas dispensing systems of the type in which pulsed doses of a respirating gas such as oxygen are supplied to a patient with breathing difficulties are provided with means to generate electricity from energy extracted from the expanding gas rather than relying solely upon batteries for power to operate the system. A pneumatic motor, which may be integral with the system dose metering means, is powered by expanding gas and drives an electrical generator to produce sufficient electricity to at least supplement that required for system operation allowing for an increase in the service time per fill or a decrease in system weight or both.

14 Claims, 3 Drawing Sheets

METHOD AND MEANS FOR POWERING PORTABLE OXYGEN SUPPLY SYSTEMS

TECHNICAL FIELD

This invention relates to methods and means for powering the operation of portable systems for supplying pulsed doses of supplemental oxygen or other respirating gases to patients.

More particularly, this invention relates to methods and means for extracting energy from stored gases to power the inhalation sensors and oxygen dispensing valves employed in those portable devices used to enrich with oxygen the respired air of a patient.

BACKGROUND ART

Physicians commonly prescribe supplemental oxygen to enrich respired air for those patients whose pulmonary systems cannot extract sufficient oxygen from ambient air. Systems to provide oxygen enrichment include a supply of oxygen, stored either as a cryogenic liquid or as a pressurized gas, and a metering device to regulate flow of oxygen to the patient. Such systems are frequently portable to permit patient mobility during treatment. The more sophisticated systems also include an inhalation sensor and dose dispensing apparatus which conserves oxygen by supplying it only while the patient is inhaling. Conservation of oxygen in this manner serves to significantly reduce the system weight as a smaller quantity of oxygen is needed for any given service time as compared to those systems employing a continuous flow of oxygen to the patient. Because of the physical limitations of breathing impaired patients it is essential that portable systems be kept as light and as small as possible.

Those systems which employ a dose dispensing apparatus to supply oxygen only while the patient is inhaling have come to be known as pulse dose devices. Typically these devices operate by sensing the beginning of an inspiration and delivering pulses or doses of oxygen at a relatively high rate beginning at the start of inspiration and lasting only for a small part of the inspiration period after which the rate is reduced to some lesser value or to zero. The sensors and control circuitry for such devices are ordinarily powered by electricity and require a current source such as a battery. Also, the valves used to control oxygen flow are usually electrically operated solenoid valves.

Pulse dose oxygen systems known in the prior art fall generally into two types; one type employing rate-time metering and the other type employing volumetric metering. An example of a rate-time metering device is that described in the Durkan et al U.S. Pat. No. 4,462,398. That device employs an electrically operated solenoid valve controlled by a timer circuit in line with a flow controlling orifice. A sensor, which may be a pressure-to-electric switch or a strain gage bridge circuit such as is employed in Honeywell's 170PC series pressure sensors, detects the onset of an inhalation. That causes the timer circuit to activate the solenoid valve for a predetermined interval thereby delivering a sized dose of oxygen to the patient. Volumetric metering devices employ a chamber sized to release a single dose quantity of oxygen through a solenoid valve which is caused to open in response to a signal indicative of the onset of an inhalation. Examples of volumetric metering systems known in the prior art are shown in applicant's U.S. Pat. Nos. 4,705,034 and 5,005,570.

All portable pulse dose delivery systems require enough electrical storage capacity to supply the needs of the system to operate the sensor, the control system and the solenoid valves which control gas flow for that time period required to deplete the supply of oxygen carried by the system. It is common practice in the art to use batteries which are periodically recharged or replaced to supply the electrical storage capacity for the system. The battery capacity required adds significantly to the bulk and weight of a portable system.

The supply of oxygen for all portable pulse dose systems is stored under pressure to provide greater storage density and to provide the motive power for dispensing it. Oxygen when stored as a gas is normally pressurized to hundreds of pounds per square inch. When stored as a cryogenic liquid, oxygen is maintained at a pressure typically ranging from about 20 to 50 psig by a relief valve which vents normal evaporation from the storage tank at that pressure. Pressurized liquid is vaporized and superheated at storage pressure before being metered and delivered to the patient. The energy of the gas expanding between storage pressure and ambient atmospheric pressure is presently wasted except for that small amount needed to expel and deliver it.

With this background it may readily be appreciated that a reduction in size and weight of systems for supplying supplemental oxygen to ambulatory patients would provide substantial advantage.

DISCLOSURE OF THE INVENTION

This invention provides a method and apparatus to harness a portion of the gas expansion energy presently wasted in the operation of systems which dispense supplemental oxygen to patients to provide at least a part of the electrical energy needed to operate the sensing, metering and delivery functions of those devices. A pneumatic motor means powering an electricity generating means is incorporated in the gas flow path in a way which does not interfere with the metering and dispensing functions of the system.

Hence, it is an object of this invention to provide a method and means for augmenting the electrical supply of a system for supplying supplemental oxygen to ambulatory patients.

It is another object of this invention to generate at least a portion of the energy required to operate a pulse dose oxygen supply system from the potential energy of the stored gas.

Other objects of the invention will be apparent from the following description of certain exemplary embodiments thereof.

DESCRIPTION OF THE DRAWINGS

Specific embodiments of the invention are illustrated in the drawings in which.

MODES FOR CARRYING OUT THE INVENTION

Figure 1:
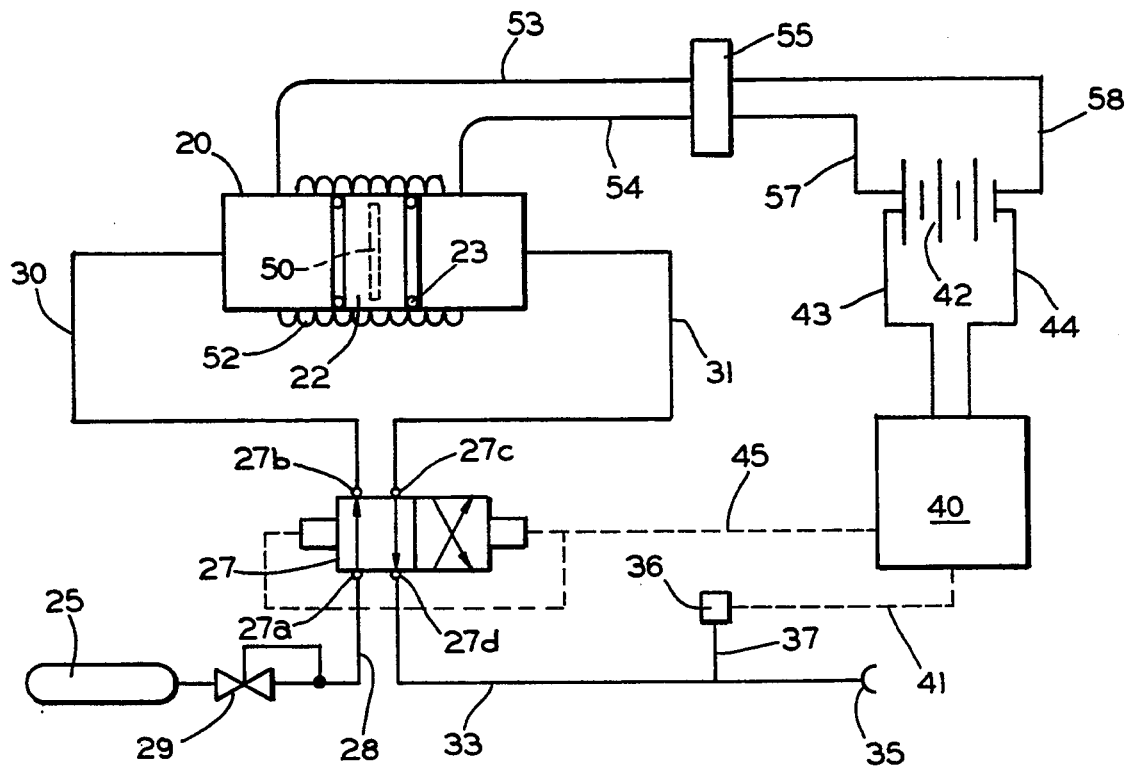
FIG. 1 depicts a volumetric pulse dose metering system in which the reciprocating displacement piston is modified to also function as a motor-generator.

A number of different embodiments of this invention will be described and discussed with reference to the drawing figures in which like reference numerals refer to the same component or part illustrated in the various figures.

Referring first to FIG. 1, there is shown an embodiment of this invention adapted for use with a pulse dose oxygen dispensing system employing a reciprocating piston such as that one disclosed in the inventor's prior U.S. Pat. No. 4,705,034. The oxygen dispensing system includes a metering displacer comprising a closed cylinder 20, shown schematically in section, and having a piston 22 disposed therein. Piston 22 preferably has sealing rings or gaskets 23 to minimize gas leakage between the piston and the cylinder walls and is free to reciprocate back and forth from one end of cylinder 20 to the other. Cylinder 20 and piston 22 are sized relative to each other such that the free space within the cylinder is equal to the unit dose administered to the patient.

The system includes a supply of respirating gas, usually pure oxygen, held as a gas under high pressure or as a cryogenic liquid in container 25. A multi-ported, two position flow control and reversing valve 27 is sited between the oxygen source 25 and displacer cylinder 20. While a four-port, two-position valve is shown in the drawing, any functional equivalent thereof may be used instead as is more fully illustrated in prior U.S. Pat. No. 5,005,570. Valve 27 is arranged with valve actuators, typically solenoids, to be movable between the two positions diagrammed. In a first valve position shown, inlet port 27a is connected to oxygen source 25 by way of line 28 through pressure regulator 29. Regulator 29 ensures that gas delivered through line 28 is maintained at a relatively constant pressure, typically ranging from 20 to 50 psig, so that the dose size delivered to the patient does not vary. Valve outlet port 27b communicates with the interior of cylinder 20 at one end thereof by way of line 30. A second line 31 provides fluid communication between the interior of cylinder 20 at the other end thereof and valve port 27c. The opposite valve port, 27d, connects to line 33 leading to cannula 35.

An extremely responsive sensor 36, which may be for example a pressure-to-electric switch or a strain gage bridge circuit, is arranged in communication with cannula 35 by way of branch conduit 37 and line 33. Sensor 36 responds to slight changes in pressure occurring at the onset of an inhalation of a patient using the oxygen supply system. That response triggers a signal, typically an electrical pulse, which is delivered to system control means 40 over transmission means 41. Control means 40 is provided with a source of electrical power which may conveniently comprise battery 42 which is connected to means 40 through conductors 43 and 44. Upon receiving a signal from sensor 36, control means 40 acting through transmission means 45 causes valve 27 to reverse positions In conventional operation with valve 27 in the position shown, oxygen from container 25 flows freely through line 28, across valve 27, through line 30 and into the interior of cylinder 20 at the left end thereof. The force of that gas, at the pressure set by regulator 29, forces piston 22 to the right driving before it the gas contained in the cylinder in the space to the right of the piston. That gas forced from the cylinder flows through line 31, across valve 27, through line 33 to cannula 35 where it is delivered for breathing by the patient. Piston 22 continues its travel until it reaches the right end of the cylinder where it stops. At that point, the entire void space of cylinder 20 to the left of the piston is filled with oxygen at the pressure set by regulator 29 and the contained oxygen is equal to a single unit dose.

A signal is passed from the sensor to the control means 40 as soon as sensor 36 detects the onset of the patient's next inhalation. That signal prompts control means 40 to power a solenoid actuator of valve 27 causing the valve to move from its first position diagrammed on the left half of the valve to its second position diagrammed on the right of the valve. Movement of valve 27 from its first to its second position reverses the directions of gas flow through the valve. At the second valve position, line 30 is connected to line 33 and thence to cannula 35 while line 31 is connected to line 28 leading to the oxygen source in container 25. Piston 22 is then rapidly forced to the left end of cylinder 20 by the pressure of oxygen entering the cylinder from the right. A measured dose of oxygen which had been held in the cylinder free space to the left of the piston is thereby delivered to the patient while a new measured dose of oxygen is stored in the cylinder free space to the right of the piston. When sensor 36 next detects the onset of an inhalation, valve 27 is caused by control means 40 to return to its original position and the cycle begins anew.

In this first embodiment of the invention, piston 22 is modified so as to have a strong permanent magnet 50 embedded therein. An annular coil 52 made of multiple turns of a conducting wire is arranged around cylinder 20 in the mid-section thereof as is shown. The wall of cylinder 20 necessarily is constructed of nonmagnetic material, suitably plastic. Conducting wires 53 and 54 comprising the two coil ends are connected to rectifier 55 which in turn is connected to battery 42 through conductors 57 and 58.

As piston 22 with embedded magnet 50 moves in response to a change in the position of valve 27 it acts in effect as a motor-generator inducing a full wave AC pulse in the surrounding coil 52. That power pulse is fed to a full-wave rectifier 55 to produce pulses of DC power which may be used to operate other components of the system. The energy in the DC power pulses may also be stored using either a rechargeable battery 42 or a capacitor (not shown) as the storage device. The control means, sensor and valve actuator are then powered from current supplied by the battery or other electrical energy storage means which need only be large enough to serve as surge storage rather than as a supply for the long term power needs of the system.

Figure 2:
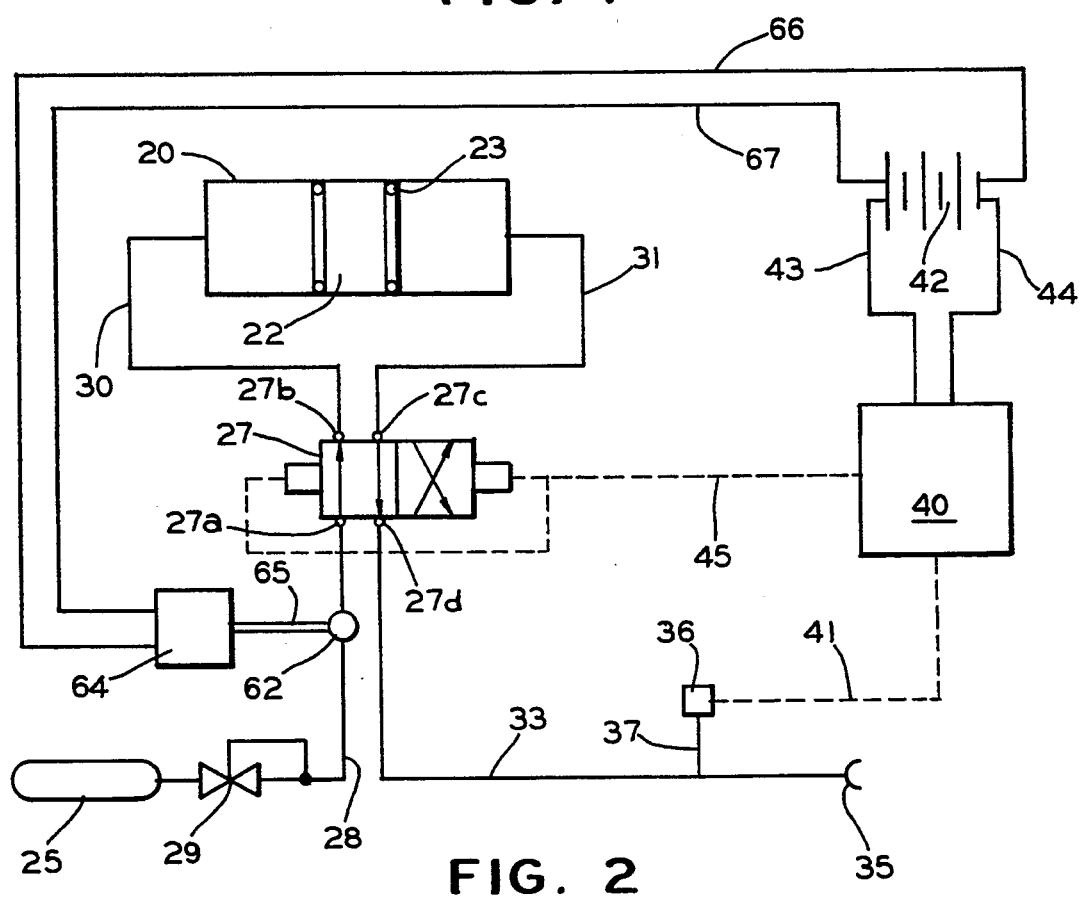
FIG. 2 illustrates the volumetric pulse dose metering system of FIG. 1 utilizing a pneumatic motor upstream of the metering cylinder.

Another embodiment of this invention is shown in FIG. 2. Here, a volumetric pulse dose oxygen supply system such as that illustrated in FIG. 1 utilizes a pneumatic motor 62 placed in gas supply line 28 upstream of the metering cylinder 20. Motor 62 is mechanically coupled to an electric generator 64 by way of connector 65 which may be gearing, a belt, a flexible shaft or similar means. The motor may comprise any conventional means for converting the force of flowing gas into rotary or linear movement. For example, motor 62 may be of the type in which the force of moving gas spins a propeller or turbine, or it may be a positive displacement motor utilizing vanes, bellows, or pistons to expand gas and convert the energy thereof into rotary or linear motion. Generator 64 may employ magneto-electric means to produce either direct current or pulsed alternating current. As shown in this Figure, generator 64 produces direct current which is conveyed to battery 42 by way of conductors 66 and 67. If the generator is arranged to produce an alternating current, then the generator output must then be rectified in the manner illustrated in FIG. 1 to obtain a pulsed direct current suitable for charging a battery or powering other components of the oxygen supply system. Other means for generating electrical power from mechanical motion, such as piezo-electric means, may be used instead of the magneto-electric means previously described. For example, the electric generator 64 may be a piezoelectric generator consisting of a piezoelectric crystal which is periodically stressed by the pneumatically operated motor. Such crystals, which are well known and commercially available, produce an electric impulse as they are struck or stressed.

Figure 3:
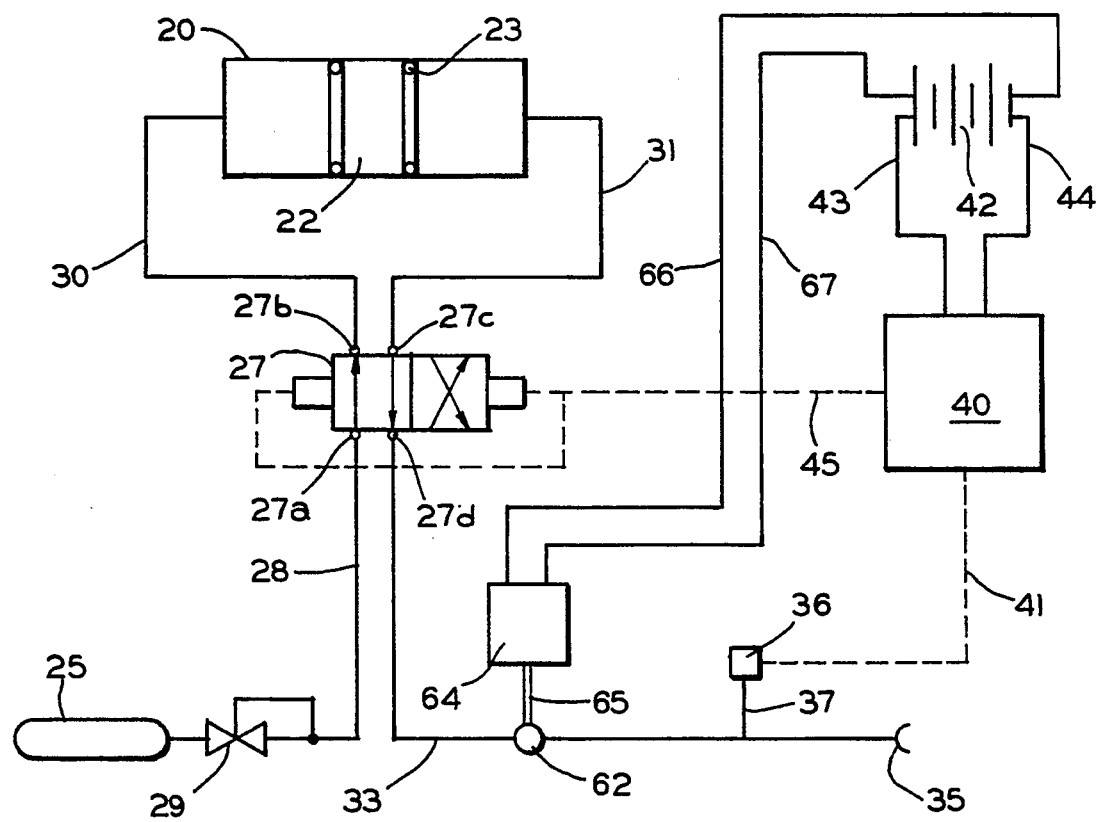
FIG. 3 illustrates the volumetric pulse dose metering system of FIG. 1 utilizing a pneumatic motor downstream of the metering cylinder.

FIG. 3 depicts a system essentially identical to that of FIG. 2 except that pneumatic motor 62 is positioned in line 33 downstream of control valve means 27. As with FIG. 2, motor 62 may be of any conventional type and is connected to generator 64 to produce an electrical current which is used to power the needs of the oxygen supply system.

Figure 4:
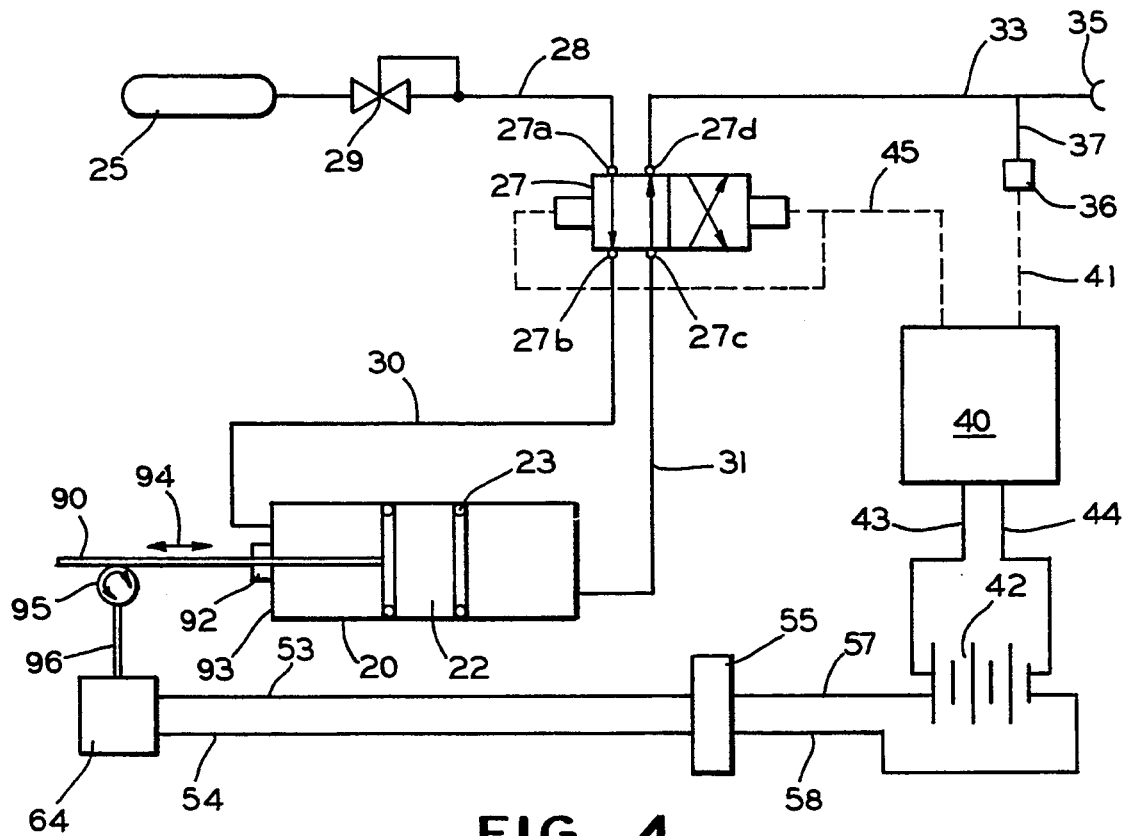
FIG. 4 shows the energy recovery system of this invention used with a pulse dose oxygen system employing rate-time metering.

FIG. 4 depicts yet another embodiment of this invention. The pulse dose oxygen supply system here is essentially that illustrated in FIG. 1 except that displacer cylinder 20 and piston 22 have been modified so as to mechanically couple piston movement to generator 64. A rod 90 is attached to one end of piston 22 and is extended through a seal 92 in an end 93 of cylinder 20. The rod 90 reciprocates back and forth as shown by arrows 94 during the operation of the oxygen supply system. A surface of rod 90 engages wheel means 95 either through frictional contact or gearing to rotate the wheel as the rod moves back and forth. Wheel means 95 is in turn connected to generator 64 through coupling means 96 thereby generating pulses of current of alternating polarity as the direction of rod movement changes. That pulsed current is conveyed to rectifier 55 by way of conductors 53 and 54 and the resulting pulses of direct current are fed to battery 32 by way of conductors 57 and 58 in the manner described in relation to FIG. 1.

Figure 5:
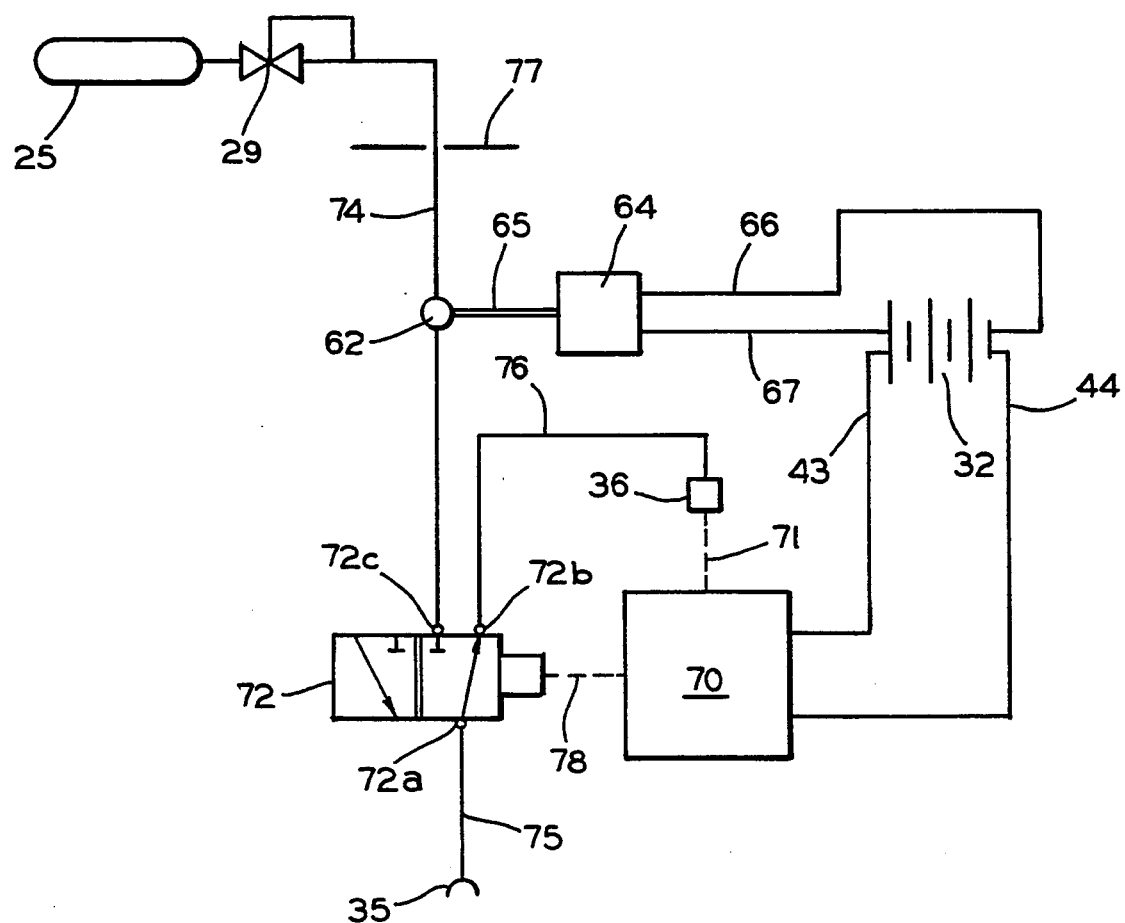
FIG. 5 depicts another embodiment of the invention used with a reciprocating piston displacer of another type.

FIG. 5 illustrates the use of this invention with a pulse dose oxygen system of the rate-time metering type. As in the embodiment of FIG. 1, this system employs a sensor 36 which produces a signal in response to slight changes in pressure occurring at the onset of an inhalation of a patient using the oxygen supply system. That signal is transmitted from sensor 36 to timer-valve control means 70 by way of transmission means 71. A flow control valve 72, activated by a timer-valve control means 70, is interposed between oxygen source 25 and cannula 35. Valve 72 communicates with oxygen source 25 by way of conduit 74 and with cannula 35 by way of conduit 75. Another conduit 76 connects valve 72 with sensor 36. The flow of gas through conduit 74 is set at a desired rate by orifice means 77 which may comprise a simple orifice or may also incorporate other functions such as a flow rate indicator.

Following operation of the system through one complete respiratory cycle, valve 72 may conveniently comprise a three port, two position valve as is diagrammed. In the valve position shown, common port 72a is connected to conduit 75 leading to cannula 35. Port 72a communicates with port 72b which in turn connects to conduit 76 leading to sensor 36. The remaining port, 72c, is blanked off in this valve position. A slight negative pressure wave produced at the onset of a patient's inhalation is transmitted from cannula 35 through conduit 75, across valve 72, along conduit 76 to sensor 36 causing the sensor to generate a signal. That signal, which may be in the form of an electrical or pneumatic pulse, is then passed to timer-valve control means 70 by way of transmission means 71. Means 70, responding to the signal and acting through transmission means 78, causes valve 72 to move to the other of its positions. In that second or other position, diagrammed on the left side of the valve, port 72c is connected to common port 72a while port 72b is now blanked off. That valve position results in open communication between oxygen source 25 and cannula 35 allowing oxygen to flow freely from the source to the patient at a rate set by orifice 77. Valve 72 is held in the second position for a length of time governed by timer-valve control means 70 and at the end of that preset time the valve is returned to its original position. Cannula 35 is then again in communication with sensor 36 and the cycle restarts when the sensor again detects the onset of an inhalation.

Valve 72 ordinarily is solenoid operated and spring biased to its first position; that one diagrammed in the drawing. That being the case, the solenoid must be activated and drawing current during all times that the valve is in its second position. Consequently, electricity requirements to operate such a valving system are quite high. Electrical power for the timer-valve control means 70 is provided by battery 32 to which it is connected through conductors 43 and 44.

In this embodiment of the invention, pneumatic motor 62 is preferably placed in line 74 between the oxygen source 25 and valve 72 but downstream of orifice 77. Metering orifices, such as orifice 77, normally operate as critical flow orifices and metered flow accuracy is less affected by a restriction downstream of the orifice than it would be if it were placed upstream. So long as the downstream to upstream absolute pressure ratio is 0.533 or less, metering accuracy will not be affected by the motor. As before, motor 62 drives a generator 64 through linkage 65 and the electrical power produced is delivered to battery 32 by way of conductors 66 and 67.

As has been illustrated and described in relation to the various embodiments, this invention provides both a method and means for harnessing a portion of the energy contained in the gas supply carried by pulse dose oxygen supply systems that is presently wasted. By harnessing that energy and converting it to electrical energy to power the system, the battery weight can be considerably reduced or the operating time of the system can be extended or both to thus enhance the utility of the systems.

Other embodiments of and uses for this invention will be apparent to those skilled in the art without departing from the spirit and scope of the following claims.

I claim:

1. An electrically powered gas dispensing system for supplying premeasured doses of respirating gas to a patient in synchronization with the patient's respiratory cycle comprising:

a supply of pressurized respirating gas;

means adapted to release sized single doses of respirating gas from said gas supply at the onset of inhalation by a patient;

conduit means for delivering said gas doses to the patient;

means for extracting energy from said gas doses as said doses flow through said conduit means from said gas supply to the patient and for converting such extracted energy to electrical energy; and means for using such electrical energy to power said dispensing system.

2. The gas dispensing system of claim 1 wherein said means for extracting energy from said flowing gas doses comprises a pneumatic motor and wherein said means for converting such extracted energy comprises means driven by said motor for generating electrical power.

3. The gas dispensing system of claim 2 wherein said means driven by said motor for generating electrical power comprises a magneto-electric generator.

4. The gas dispensing system of claim 2 and wherein said means driven by said motor for generating electrical power comprises a piezo-electric generator.

5. The gas dispensing system of claim 2 wherein said pneumatic motor is a positive displacement motor.

6. An electrically powered gas dispensing system for supplying premeasured doses of respirating gas to a patient in synchronization with the patient's respiratory cycle comprising: a supply of pressurized respirating gas; means adapted to release sized single doses of respirating gas from said gas supply at the onset of inhalation by a patient including a piston movable in a cylinder for metering said gas doses; conduit means for delivering said gas doses to the patient; positive displacement pneumatic motor means including said piston and said cylinder for extracting energy from said gas as said doses flow through said conduit means from said gas supply to the patient and for converting said extracted energy to electrical energy: and means for using such electrical energy to power said dispensing system.

7. The gas dispensing system of claim 6 wherein means driven by said motor means for generating electrical power comprises an electric generator and wherein said piston is mechanically coupled to drive said electric generator.

8. The gas dispensing system of claim 6 wherein said piston includes a magnet; wherein a coil formed of conducting wire encircles said cylinder; and wherein said magnet and coil are so arranged that an electrical pulse is induced in said coil as the piston moves within the cylinder.

9. The gas dispensing system of claim 8 including a rectifier and an electrical energy storage device, said rectifier arranged to receive alternating current pulses from said coil and to transmit direct current pulses to said electrical energy storage device.

10. In a method for operating a portable respiratory gas supply system for delivering supplemental doses of respirating gas to a patient in synchronization with the patient's respiratory cycle, said gas supply system including a supply of pressurized respirating gas, an inhalation sensor, a metering system, a flow control system and interconnecting conduits, and requiring a supply of electrical energy for its operation; the improvement comprising extracting pneumatic energy from said gas doses flowing from said respirating gas supply to a patient and using that energy to generate electricity to operate the system.

11. The method of claim 10 in which pneumatic energy is extracted from said flowing gas doses by placing a pneumatically driven motor in said interconnecting conduits downstream of said supply of pressurized respirating gas.

12. The method of claim 11 wherein electricity is generated by a generator driven by said motor.

13. A portable system for supplying measured doses of a respirating gas to a patient in synchronization with the respiratory cycle of the patient comprising:

a supply of pressurized respirating gas;

metering means comprising a piston reciprocating within a cylinder and arranged that so that movement of the piston delivers a measured dose of respirating gas;

a permanent magnet embedded in said piston;

a coil comprising multiple turns of a conducting wire encircling said cylinder at a medial point thereof;

a sensor adapted to detect inhalations of the patient and to produce signals in response thereto;

flow control means adapted to control the flow of gas into and out of said metering means in response to said signals, said flow control means including electrically operated solenoid valve means;

rectifier means connected to said coil and adapted to convert pulses of alternating current produced by movement of said piston into direct current; and means for using that direct current to power said flow control means.

14. The system of claim 13 including an electrical energy storage device having at least sufficient capacity to operate said system for the time period between the production of electricity by movement of said piston and its use to power said flow control means.

* * * * *